United States Patent [19]
Glück et al.

[11] Patent Number: 6,040,167
[45] Date of Patent: Mar. 21, 2000

[54] SYNTHETIC MEMBRANE VESICLES CONTAINING FUNCTIONALLY ACTIVE FUSION PEPTIDES AS DRUG DELIVERY SYSTEMS

[75] Inventors: Reinhard Glück, Spiegel bei Bern; Peter Klein, Langenbruck; Peter Herrmann, Liestal; Ernst Rudolf Wälti, Münchenbuchsee, all of Switzerland

[73] Assignee: Nika Health Products Limited, Liechtenstein

[21] Appl. No.: 07/930,593

[22] PCT Filed: Jan. 17, 1992

[86] PCT No.: PCT/EP92/00089

§ 371 Date: Nov. 2, 1992

§ 102(e) Date: Nov. 2, 1992

[87] PCT Pub. No.: WO92/13525

PCT Pub. Date: Aug. 20, 1992

[30] Foreign Application Priority Data

Feb. 2, 1991 [EP] European Pat. Off. .............. 91101414

[51] Int. Cl.[7] .............................. C12N 7/00; A61K 9/127; A61K 39/395; C07K 14/11
[52] U.S. Cl. ..................... 435/235.1; 424/179.1; 424/450; 435/388.1; 435/388.8; 435/389.1; 435/389.7; 435/391.1; 514/2; 530/350
[58] Field of Search ................. 424/450, 209.1, 424/1.21, 179.1; 264/4.6; 435/235.1, 388.1, 388.8, 389.1, 389.7, 391.1; 514/2; 530/350

[56] References Cited

U.S. PATENT DOCUMENTS

| | | | |
|---|---|---|---|
| 4,663,161 | 5/1987 | Mannino et al. | 424/450 |
| 4,871,488 | 10/1989 | Mannino et al. | 264/4.6 |
| 5,000,960 | 3/1991 | Wallach | 424/1.21 |

FOREIGN PATENT DOCUMENTS

| | | |
|---|---|---|
| 0047480 | 3/1982 | European Pat. Off. . |
| 0298280 | 1/1989 | European Pat. Off. . |

OTHER PUBLICATIONS

Martin et al. Irreversible coupling of immunoglobulin fragments to preformed vesicles. J. Biol. Chem. vol. 257 pp. 286–288, 1982.

Kawasaki et al., Biochimica Et Biophysica Acta 733: pp. 286–290, (1983).

Stegmann et al., Embo J. 6: pp. 2651–2658, (1987).

Poste et al; Prescott, Editor; *Methods in Cell Biology* vol. XIV. (1976), pp. 33–71, Academic Press, NY, NY.

Sizer et al, Biochemistry 26: pp. 5106–5113, (1987).

Levy et al., Biochemistry 29: pp. 9480–9488, (1990).

Vainstein et al., Biochim. Biophys. Acta 773: pp. 181–188, (1984).

Walter et al., Membrane Fusion, pp. 395–418, Marcel Dekker, Inc. (Publisher), NY, NY. (1991).

Sechoy, et al., *Experimental Cell Research 185*, pp. 122–131 (1989).

Barbet, et al., *Journal of Supramolecular Structure and Cellular Biochemistry*, 16:243–258 (1981); Cellular Recognition 237–252.

Nassander, et al., *Biochimica et Biophysica Acta*, 1235 (1995) 126–139.

D. Glick, *Methods of Biochemical Analysis*, 1988, vol. 33, pp. 424–426, Chapter E (John Wiley & Sons, New York, U.S.A.).

*Primary Examiner*—John S. Brusca
*Attorney, Agent, or Firm*—Ostrolenk, Faber, Gerb & Soffen, LLP

[57] ABSTRACT

The phospholipid bilayer contains at least one pharmaceutically active drug and comprises cell-specific markers on the membrane which have at least 90% biological activity when measured according to Luescher & Glueck, Antiviral Research 14, 39–50. In the membrane, the cholesterol content is preferably less than 2% by weight, the detergent content preferably less than 1 ppb. The vesicle diameter preferably is about 80 nm. the phospholipid in the membrane may comprise 70 to 95% by weight of phosphatidylcholine and preferably 10 to 20% by weight of phosphatidylethanolamine; preferably 6–8% by weight of a crosslinker, preferably of a sulfosuccinimidyl derivate, and at least one cell-specific fusion peptide are linked to the membrane. The vesicles are used for the preparation of pharmaceuticals against AIDS and carcinomas.

39 Claims, 3 Drawing Sheets

FIG. 1

FIG. 2

| | | |
|---|---|---|
| CCC GLFG | AIAGFIENGWEGMIDG | WYG | SEQ ID NO. 1
| GLFG | AIAGFIENGWEGMIDG | WYGCCC | SEQ ID NO. 2
| CCC GLFG | AIAGFIENGWEGMIDG | | SEQ ID NO. 3
| GLFG | AIAGFIENGWEGMIDG | CCC | SEQ ID NO. 4
| CCC GLFE | AIAGFIENGWEGMIDG | | SEQ ID NO. 5
| GLFE | AIAGFIENGWEGMIDG | CCC | SEQ ID NO. 6
| CCC ELFG | AIAGFIENGWEGMIDC | | SEQ ID NO. 7
| ELFG | AIAGFIENGWEGMIDG | CCC | SEQ ID NO. 8
| CCCLFG | AIAGFIENGWEGMIDG | | SEQ ID NO. 9
| LFG | AIAGFIENGWEGMIDG | CCC | SEQ ID NO. 10
| CCC | PPGAVIGTIALGVATAAGIT | | SEQ ID NO. 11
| | PPGAVIGTIALGVATAAGIT | CCC | SEQ ID NO. 12
| CCC | PAGVVIGLAALGVATAAGVT | | SEQ ID NO. 13
| | PAGVVIGLAALGVATAAGVT | CCC | SEQ ID NO. 14
| CCC | PIGAIIGGVALGVATAAGIT | | SEQ ID NO. 15
| | PIGAIIGGVALGVATAAGIT | CCC | SEQ ID NO. 16

SYNTHETIC MEMBRANE VESICLES CONTAINING FUNCTIONALLY ACTIVE FUSION PEPTIDES AS DRUG DELIVERY SYSTEMS

FIELD OF THE INVENTION

The invention relates to synthetic membrane vesicles (liposomes) and particularly to vesicles exhibiting on their surface fusion peptide molecules and other cell-specific proteins. The fusion peptide molecule may be in the form of a synthetic or purified peptide or as a part of a spike glycoprotein molecule of an enveloped virus, e.g. hemagglutinin, such as of influenza, parainfluenza or Semliki Forest virus. The cell-specific protein may be an IgG antibody, e.g. the CD4 antibody.

DESCRIPTION OF RELATED ART

When a drug is given to a subject it must usually pass from the site of administration in to the plasma compartment, and therefore the route of administration may have an important effect on the pharmacokinetic profile of the drug in the circulation. Thus, oral administration of the drug, while convenient, results in a slow onset of drug action and is somewhat unreliable in terms of achieving optimum plasma drug levels. By contrast, intravenous injection results in the prompt and exact establishment of circulating levels, at the cost of some pain and inconvenience to the patient. However, even if the drug is injected directly into the systemic circulation, the relationship between administered dose, drug levels and duration of the target site is by no means simple. These parameters are determined by a complex and often competing network of pathways leading either to accumulation of active drug molecules at the target site, or to the inactivation and excretion of the drug. These pathways involve biotransformation in the liver and in other tissues, excretion via the kidney or the bile, binding of drugs to fixed or circulating cells or macromolecules, and the passive or mediated passage of the drug across membrane barriers (Creasy, W. A. (1979): Drug Disposition in Humans, Oxford Univeristy Press, New York).

In recent years, there has been a good deal of interest in the prospect of influencing the distribution and metabolism of drugs in beneficial ways by using various sorts of carrier or drug delivery systems. These systems are designed to control one or more of the following parameters (Juliano, R. R. (1975), Can. J. Physiol. Pharmaco 56, 683–690):

a) the rate of input of the drug into a particular body compartment;

b) the distribution and localization of the drug in the body;

c) the persistence or rate of metabolism of the drug.

A major improvement in controlled drug delivery systems was the development of liposomes which were first described by Bangkam et al. (Bangkam, A. D., Standish, M. M. and Watkins, J. C. (1965), J. Mol. Biol. 13, 238–252). Today, the literature claims an extravagant variety of benefits to be gained by delivering particular drugs in liposomes. These can be loosely grouped under the following headings:

1. Liposomes may cross biomembranes and may facilitate the transport of drugs through normally impermeable barriers. In particular, liposomes facilitate the intracellular penetration of encapsulated compounds.

2. Liposomes may be designed to interact with specific tissues, improving drug selectivity and reducing toxicity.

3. Drug pharmacokinetics may be beneficially modified by liposomes, through modulation of drug release, distribution and removal from the systemic circulation.

4. Chemically and metabolically labile drugs may be protected by liposomes from deactivation.

Drugs of potential therapeutic interest may be sequestered in this way, the encapsulated compounds exhibiting modified properties, at least in vitro, when compared with the unmodified substances. Unfortunately, early hopes of a revolutionary new approach to chemotherapy have not been completely realised by the experimental facts (Fildes, F. J. T. (1981), Liposomes. From physical structure to therapeutic applications. Knight (ed.), Elsevier/North-Holland Biomedical Press).

A better result using liposomes as vectors could be achieved by the targetting of liposomes with specific proteins. If substances encapsulated in liposomes were to be delivered more successfully to selected organs or tissues, these targetting techniques had to be devised in order to bypass the accumulation of liposomes at undesirable sites (thus reducing toxicity) and to optimize the delivery to specific cells (thus enhancing the desired effect).

Several investigations have utilized the coating of liposomes with aggregated immunoglobulins in order to optimize delivery to phagocytic cells (Ismail, G., Boxer, L. A. and Bachner, R. L. (1979), Pediatr. Res., 13. 769–773/ Finkelstein, M. C., Kuhn, S. H., Schieren, H., Weissmann, G. and Haffstein, S. (1980): Liposomes and Immunobiology (Tom, B. H. and Six, H. R. eds.) 255–270. Elsevier/North-Holland Publishing Co., Amsterdam).

A further improvement was described by Gregoriadis and Neerunjun (1975), Biochem. Biophys. Res. Commun., 65, 537–544, whereby the targetting of liposomes was enhanced by associating cell-specific IgG antibodies. The uptake of liposomes was augmented 3- to 25-fold when different cell strains were presented with liposomes associated with IgG immunoglobulins raised against the particular cell strain. However, the technique employed showed that the liposomes targetted in this way failed to fuse with the cell membrane and therefore an efficient delivery of drugs into the cells was prevented. (Leserman, L., Weinstein, J. N., Blumenthal, R., Sharrow, S. O. and Texy, W. D. (1979), J. Immunol. 122, 585–591).

A major improvement in the production of drug delivery systems was the targetting of liposomes with viral proteins: liposomal membranes have been reconstituted with proteins such as the hemagglutinin from influenza virus (Almeida, J. D., Brand, C. M., Edwards, D. C. and Heath, T. D. (1975), Lancet 2, 899–901). The efficiency and specificity of early viral interaction with host cells (adsorption, penetration) may be conferred upon liposomal carriers by incorporating the appropriate viral proteins into the liposomal membranes. Indeed, the incorporation of Sendai virus spike proteins into liposomal bilayers produced at least a 100-fold enhancement in the uptake by mouse L cells of diphteria toxin fragment A as compared with fragment A-containing liposomes without spikes (Uehida, T., Kim, J., Yamaizumi, M., Miyahe, Y. and Okada, Y. (1979). Cell. Biol. 80, 10–20).

The main drawbacks of the above methods lie in the lack of fully active influenza hemagglutinin fusion peptides. Influenza A viruses penetrate their host cells by membrane fusion. After binding to the cell surface, virus particles are internalized and transported to endosomes and lysosomes. The acidic environment in these organelles activates fusion between the viral and host cell membranes. The advantage of vesicle-cell fusion at low pH lies in the fact that the content of the vesicles is released after internalizing into the cytoplasma of the cells (pH in the endosome is around 5.2). The discovery of this low-pH-induced fusion of influenza virus glycoproteins led to many attempts to develop effective drug delivery systems with influenza hemagglutinin targetted liposomes. Kawasaki, K. et al. (Biochemica et Biophysica Acta, (1983), 733, 286–290, used reconstituted vesicles of influenza hemagglutinin glycoproteins in egg yolk phophatidylcholine/spin-labeled phosphatidylcholine/cholesterol (molar ratio 1.6:0.4:1). Preparations at appropriate protein to lipid ratios (1:44 and 1:105 mol/mol) contained vesicles with a diameter of 100–300 nm and a high densitiy of spikes on the surface, but have several drawbacks:

1) Due to the high cholesterol content and a residue of detergent, they show reduced endocytosis by phagocytic cells. Kawasaki et al themselves report only a 66% activity; but according to a more recently developed, improved test method, the activity is only 1% after 7 minutes (see Example 10 below). This might be due to the fact that Triton X-100 used by Kawasaki et al partially reacts with hemagglutinin and is not completely removed by dialysis.

2) To study the role of the viral membrane components in the fusion reaction in detail, it is necessary to be able to manipulate these components. For this purpose a method is required for the isolation and reconstitution of the viral spike proteins, producing reconstituted virosomes with full biological fusion activity. Despite the efforts of Kawasaki et al., reconstitution of influenza virus envelopes, displaying full biological fusion activity, has not been reported.

3) The attachment of the targetted liposomes containing pharmaceutical active drugs to specific cells could not be demonstrated.

Most of the other methods that have been employed to reconstitute viral envelopes are based on solubilization of the viral membrane with a detergent and, after sedimentation of the internal viral proteins and genetic material, removal of the detergent from the supernatant. Detergents with a high critical micelle concentration, such as octylglucoside, may be removed effectively by dialysis. Reconstitution employing octylglucoside has been reported for Semliki Forest virus (SFV) (Helenius, A., Sarvas, M. and Simons, K. (1981), Eur. J. Biochem. 116, 27–35); vesicular stomatitis virus (VSV) (Eidelman, O., Schlegel, R., Tralka, T. S. and Blumenthal, R. (1984), J. Biol. Chem. 259, 4622–4628); influenza virus (Huang, R. T. C., Wahu, K., Klenk, H. D. and Rou, R. (1980) Virology, 104, 294–302); and Sendai virus (Harmsen, M. D., Wilschut, J., Scherphof, G., Hulstaert, C. and Hoekstra, D. (1985), Eur. J. Biochem., 149, 591–599). However, properly reconstituted viral envelopes were not produced in all cases. For example, virosomes formed from SFV had a protein to lipid ratio deviating from that of the viral membrane, and virosomes produced from VSV did not exhibit biological fusion activity.

Another method, described in the literature, is the detachment of influenza viral spikes from the virus particles with bromelain. The hemagglutinin recovered in such a way was attached to liposomes (Doms, R., Helenius, A. and White, J. (1985), J. biol. Chem., 260 (5) 2973–2981). The main drawback of this method is the limited biological activity of such vesicles due to the cleavage by bromelain.

SUMMARY OF THE INVENTION

Thus, the technical problem underlying the present invention is to provide vesicles which transport desired drugs or pharmaceutically active substances to specific cells, such as macrophages, T4-helper cells, brain cells or other cells of specific organs, which then are fully attached to these cells, internalized by phagocytosis or endocytosis so as to immediately after endocytosis—deliver the desired drug into the cytoplasma of the desired cell.

The solution to the above technical problem is achieved by providing the vesicles which are characterized by being a phospholipid bi-layer vesicle comprising cell-specific markers on the membrane and containing at least one pharmaceutically active drug where the cell-specific markers have at least 90% biological activity when measured according to Luescher & Glueck, Antiviral Research 14, 39–50. Specific embodiments of the invention and improved vesicles are described. A process for the preparation of such vesicles is described and uses of such vesicles are also described.

Accordingly, vesicles are provided which contain a liposome ideal for endocytosis and a biologically fully active cell-specific marker, preferably a viral hemagglutinin glycoprotein or a derivative thereof, or a synthetic fusion peptide being capable of inducing the immediate fusion of said vesicles after endocytosis by the desired cells.

In another embodiment of the invention, a suitable crosslinker which adsorbs to the specific liposome is used in the mixture together with a specific antibody, directed to the responsible receptor of the desired cell for inducing the endocytosis mechanism, which is bound to the crosslinker in such a manner that it is still fully biologically active.

In another embodiment, the invention provides a phospholipid bilayer vesicle having at least one desired drug or pharmaceutically active substance therein, said vesicle comprising; (a) a membrane having one or more viral phospholipids in combination with other phospholipids comprising phosphatidylethanolamine (PE); (b) at least one active fusion peptide that is a non-Sendai viral hemagglutinin that causes the vesicles to be internalized by target cells through phagocytosis or endocytosis, said hemagglutinin being attached directly or indirectly to said membrane; (c) a bifunctional crosslinker linked to phosphatidylethanolamine (PE) of said membrane; and (d) at least one cell-specific marker linked via its sulphur to the PE-bound crosslinker, said marker being a biologically active protein for binding to a receptor of target cells In some preferred embodiments, the membrane includes 5 to 20% by weight of viral phospholipids and 80 to 95% by weight of other phospholipids, based on total phospholipids, wherein said other phospholipids comprise 5 to 90% by weight of phosphatidylcholine and 5 to 30% by weight of phosphatidylethanolamine, based on total phospholipids; and 5 to 10% by weight of said bifunctional crosslinker.

BRIEF DESCRIPTION OF THE DRAWINGS

FIG. 1 shows the principle of the procedure for the preparation of the vesicles of the instant invention; a circle designates a liquid solution or suspension; a square designates a solid pellet or precipitate;

FIG. 2 provides a diagram of amino acid sequences (Seq. ID Nos. 1–16) which may be used as crude fusion peptides instead of influenza hemagglutinin trimers; and FIG. 3 shows the kinetics of fluorescence dequenching of R18-labelled influenza A virus with DOPC-cholesterol liposomes. The increase in fluorescence is expressed in % FDQ (fluorescence dequenching), calculated according to L üscher & Glück (see herein). Curve 2 corresponds to the fusion activity of vesicles prepared according to the method of Kawasaki et al.

PREFERRED EMBODIMENTS OF THE INVENTION

The essential feature of these drug delivery vesicles is that they carry on their surface said fully active viral glycoproteins or a derivative thereof and biologically active, specific antibodies being capable of attaching to the desired cells, of being internalized by phagocytosis or endocytosis by these cells, inducing the immediate fusion of said vesicles with internal cytoplasmic membranes and releasing the virosome's content into the cytoplasma of these cells. Due to the fully active fusion peptides of the present invention, the drugs are released immediately after phagocytosis so as to avoid an undesired long stay in the endocytosomes which would give rise to unspecific degradation of the pharmaceutical substances contained in the viral hemagglutinin vesicles of the present invention. At pH 5, the influenza fusion peptides on the surface of the vesicles are activated in the same way as is the case with live influenza virus. The content of the vesicles is released into the cytoplasm, as is the case with influenza virus and the released nucleoprotein.

The term "liposome" refers to medium sized bilamellar phospholipids prepared by controlled detergent removal. The size of the vesicle initially formed upon detergent removal depends on the detergent and phospholipid used and, in some cases, on the method and rate of detergent removal.

The present invention also relates to a method of preparing vesicles which are specially suited for phagocytosis. It comprises the following steps:

1) Dissolution of one or two phospholipids in a non-ionic detergent solution particularly in a detergent solution that has a concentration of between 10 and 250, preferably between 80 and 120 $\mu$mol octaethylene glycol monododecylether (OEG) per ml fusion buffer;

2) vesicle formation through detergent removal with polystyrene beaded micro-carriers (mesh size—wet—20–50;

3) a defined mechanical movement is performed during detergent removal;

4) the desired diameter of vesicles (50–100 nm) is achieved by ultrasonification.

In still another embodiment, the present invention refers to vesicles comprising phospholipids from at least one member of the group consisting of influenza virus, preferably from the A-$H_1N_1$ subtype, rhabdovirus, parainfluenza virus, and togavirus, in combination with a 2 to 100-, preferably 5 to 15-fold quantity of phosphatidylcholine, and preferably to vesicles where the phospholipid in the membrane comprises 70–95% phosphatidylcholine and 5–30% preferably 10–20% by weight of another phospholipid, such as phosphatidylethanolamine. The cholesterol content is preferably less than 1%.

The term "fusion peptide" refers to viral spike glycoproteins containing the fusion peptide. In one embodiment, the present invention refers to the complete hemagglutinin trimer of viral surface spikes or to one monomer or to one or both cleaved subunits, the glycopeptides HA1 and HA2, containing the functional fusion peptide. In another embodiment, the present invention refers to the fusion peptide itself, isolated or synthetically produced. In a particularly preferred embodiment of the present invention, these polypeptides, containing the fusion peptide, refer to influenza hemagglutinins, especially the one of the A-$H_1N_1$ subtype.

The term "crosslinker" refers to an organic heterofunctional molecule capable of linking to the surface of vesicles prepared according to this invention and capable of binding polypeptides. In a preferred embodiment of the present invention, this molecule is an organic, bifunctional molecule containing a carboxylic group and a thiol group, particularly a sulfosuccinimidyl-(S-)derivate, such as S-4-(p-maleimidophenyl)butyrate, S-acetate, S-2-(m-azido-o-nitrobenzamido) ethyl-1,3'-dithiopropionate, S-6-(4'-azido-2'-nitrophenylamino)hexanoate S-(4-azidophenyldithio) propionate, S-2(p-azidosalicylamido)ethyl-1,3'-dithiopropionate, S-2-(biotinamido)-ethyl-1,3'-dithiopropionate, S-6-(biotinamido) hexanoate, S-3-(4-hydroxyphenyl)propionate, S-(4-iodoacetyl)aminobenzoate, S-4-(N-maleimidomethyl)cyclohexane-1-carboxylate, S-2, 2,5,5-tetramethylpyrroline-1-oxyl-HCl.

The term "cell-specific" protein or marker refers to a protein capable of linking to the crosslinker at the vesicle's surface and linking to the receptor of cells inducing the endocytosis mechanism. In a preferred embodiment of the present invention, this molecule refers to a cell receptor specific antibody, particularly to a monoclonal antibody.

The examples and figures illustrate the invention:

EXAMPLE 1

Preparation of synthetic membrane vesicles of phosphatidylcholine with fully functionally active viral fusion peptides in a hemagglutinin trimer from influenza virus and containing dextran sulfate as antiviral drug.

Figure 1:
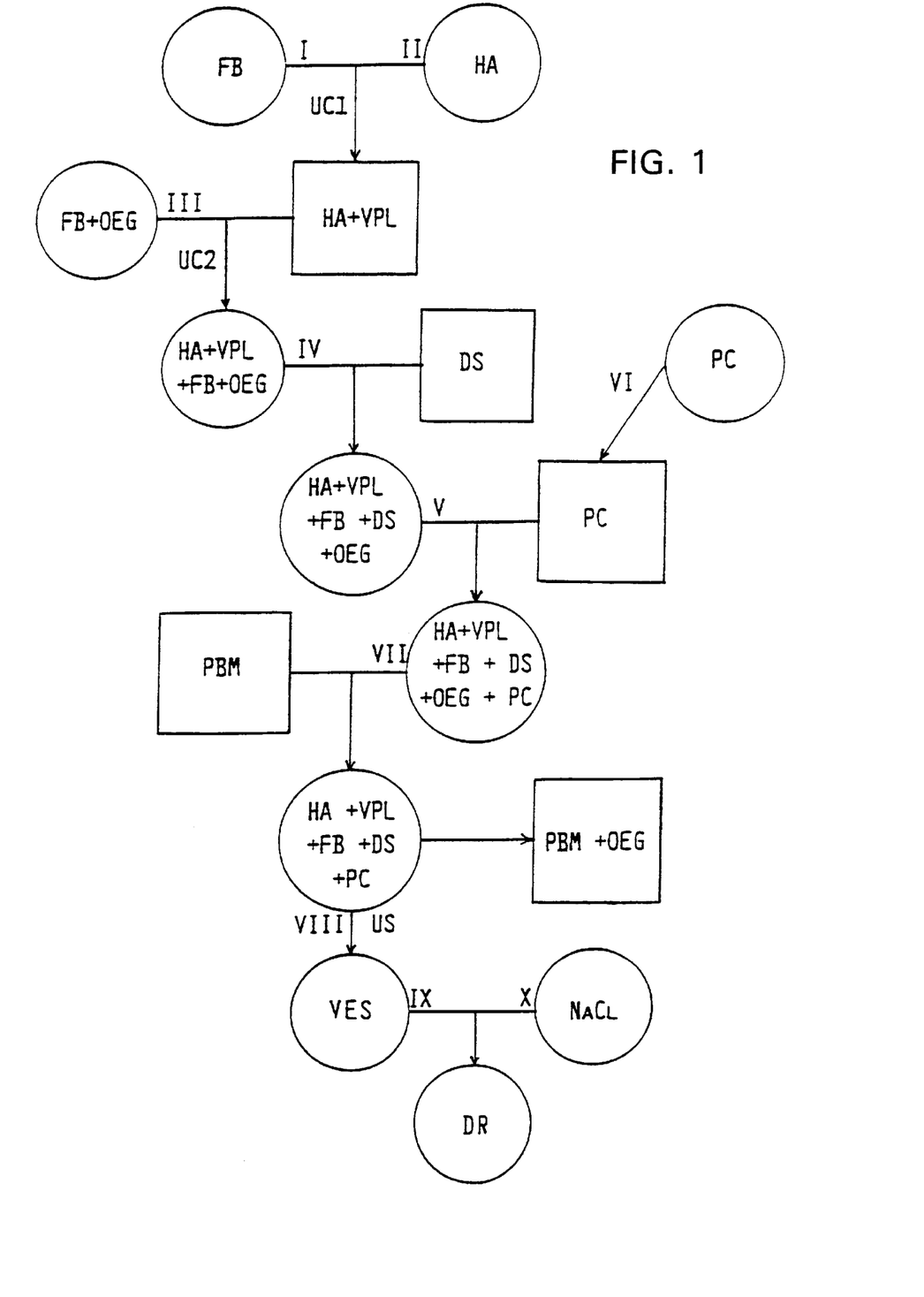

FIG. 1 shows the principle of the procedure; a circle designates a liquid solution or suspension; a square designates a solid pellet or precipitate. In general:

A fusion buffer solution FB containing 2700 mg solids and a hemagglutinin suspension HA containing 46 mg HA and 31.1 $\mu$mol viral phospholipids VPL were mixed and subjected to ultracentrifugation UC1. The resulting pellet was dissolved in solution III containing fusion buffer FB and octaethylene glycol monododecyl ether OEG as a mild detergent. Another ultracentrifugation UC2 yielded a supernatant IV containing FB, HA, VPL and OEG, to which was added the antiviral drug dextran sulfate DS to make up a solution V. In the meantime, a phosphatidylcholine (PC) solution VI was vacuum dried in a rotating round-bottom flask producing a thin PC layer on the inner surface of the flask. Solution V was added to this layer and dissolved it to a solution VII which was treated three times with polystyrene beaded microcarriers PBM to remove the OEG and to result in a solution VIII, in which—by ultrasonification US—vesicles VES of the desired size were developed; the resulting suspension IX was diluted with NaCl solution X to give the drug suspension DR.

In detail:

A fusion buffer solution (I) was prepared containing 7.9 mg NaCl/ml, 4.4 mg/ml trisodium trisodiumcitrate dihydrate, 2.1 mg/ml 2-morpholinoethane sulfonic acid monohydrate (MES), and 1.2 mg/ml N-hydroxyethyl-piperazine-N'-2-ethane sulfonic acid in $H_2O$ (pH adjusted with 1-N NaOH to 7.3).

Influenza virus (strain A/Shanghai/16/89 (H3N2)) was grown in the allantoic cavity of hen eggs, and was purified twice by ultracentrifugation in a sucrose gradient, as described by Skehel and Schild 1971 (Virology 44, 396–408). The purified influenza virion suspension (II) contained 266 $\mu$g of influenza virus hemagglutinin per ml and a total of 31.1 $\mu$mol of viral phospholipids, which were determined as follows:

Viral phospholipids were extracted according to Folch et al. (Folch, J., Lees, M. and Sloane, S. G. H. (1957); J. Biol. Chem. 226, 497–509). For analysis of phospholipids, the lower organic phase was evaporated and the residue either subjected to phosphate determination (Chen, P. S., Toribara, T. Y. and Warner, H. (1956); Anal. Chem. 28, 1756–1758), or dissolved in a small volume of chloroform-methanol for subsequent TLC analysis of the phospholipids. Silica gel plates (Merck) were used and were developed in the solvent system chloroform-methanol-acetic acid-water (25:15:4:2; v/v/v/v). The individual phospholipids were visualized by exposure to iodine and were identified on the basis of their RF values (comparison with reference samples). Protein was determined by a modified Lowry procedure (Peterson, G. L. (1977); Anal. Biochem. 83, 346–356).

A total of 173 ml of solution (II) was mixed with the same volume of said fusion buffer solution (I). This influenza virus dilution was pelletted by ultracentrifugation at 100,000×g for 10 minutes.

15.3 ml of a detergent solution containing 54 mg/ml (=100 µmol/ml) of octaethylene glycol monododecyl ether (OEG) in said fusion buffer solution was added to the influenza virus pellet. This corresponds to 18 µg=33.3 nmol OEG per µg hemagglutinin. After 10 minutes, the pellet was completely dissolved. The solution was subjected to a 1 hour ultracentrifugation at 100,000×g. 3000 mg of the dried antiviral drug dextran sulfate (Lüscher, M. and Glück, R., Antiviral Research 14, 39–50) were added to the remaining supernatant IV containing the solubilized influenza hemagglutinin trimer plus the non-essential neuraminidase residue and other constituents, making up solution V.

Phosphatidylcholine (SIGMA) was dissolved in a 2:1 mixture of chloroform and methanol to a concentration of 10 mg/ml. 28 ml of this solution VI were carefully evaporated by applying a vacuum in a rotary evaporator, forming a thin phospholipid layer of 280 mg on the inner surface of a round-bottom flask.

The solution V was now added to the phospholipid layer in the round-bottom flask. After shaking for at least 15 minutes and complete dissolution of the phosphatidylcholine, the resulting solution VII was transferred to a glass container together with 4.8 g of polystyrene beaded microcarriers PBM having a mesh size (wet) of 25–50.

The container was then shaken in such a way that the content moved twice per second from one end to the other. One hour later, the suspension was aspirated with a thin pipette and transferred to a new container with 2.4 g of polystyrene beaded microcarriers of the same size. The column was shaken for 30 minutes. This procedure was repeated twice. After the last step, the resulting solution VIII was removed from the beads, fixed in a waterbath and treated with an ultrasonification apparatus (Bransonic, Branson Europe BV, frequency 50 kHz±10%). 10 seconds of ultrasonic shocks repeated twice, after intervals of 10 seconds each, yielded medium sized vesicles with a diameter of about 50–100 nm. The final solution IX was then diluted 1:100 with physiological NaCl solution X.

EXAMPLE 2

Preparation of synthetic membrane vesicles containing an antiviral antibody drug adsorbed with hemagglutinin trimers of influenza virus and CD4 monoclonal antibodies.

The vesicles were prepared according to Example 1 with the following modification: instead of 10 mg, only 9 mg of phosphatidylcholine, and 1 mg of phosphatidylethanolamine (kephaline) per ml were dissolved in a 2:1 mixture of chloroform and methanol.

After the preparation of hemagglutinin vesicles according to Example 1, 20 mg of sulfosuccinimidyl-4-(N-maleimidophenyl)butyrate (SMPB) (as a crosslinker) in 2 ml of water were added to the solution. After 1 hour at room temperature under gentle shaking, the vesicles were pelletted by ultracentrifugation during 10 min at 100,000×g.

8 ml of Anti-Leu 3A (Becton & Dickinson) were added to the pellet. The resuspended material was carefully shaken for a few seconds every 5 minutes during one hour at room temperature. Finally, the material was pelletted again (to remove non-bonded antibodies) by ultracentrifugation at 100,000×g for 10 minutes. The pellet was resuspended in 1,500 ml of physiological NaCl solution.

EXAMPLE 3

Example 2 was repeated with the following modifications:

Instead of dextran sulfate, 1000 mg each of imidazol-carboxamide and hydroxy-urea (pharmaceuticals efficient against melanomas as described by Brunner and Nagel, Springer Verlag, 2nd edition, Internistische Krebstherapie, page 93 (1979)) were added to the solution IV (see Example 1).

After adding the crosslinker and further processing as in Example 2, 1 mg of a monoclonal antibody (either R 24 as described by Houghton, A. N. et al. (1985), Proc. Nat. Ac. Sc. Vol. 82, p. 1242; or 0.5 mg L55+0.5 mg L72 as decribed by Iric, R. S. et al., Lancet (1989), p. 786–787) were added to the vesicle solution VES to result in the following total composition for 1000 human doses:

46 mg hemagglutinin 250 mg phosphatidylcholine 30 mg phosphatidylethanolamine (kephaline)

20 mg crosslinker (Sulfo-SMPB)

1 mg monoclonal antibody 1000 mg imidazol-carboxamide 1000 mg hydroxy-urea

These pharmaceuticals so far conventionally had to be applied in about 5-fold quantitative dosage, i.e. the indicated quantities are for 200 human doses only.

EXAMPLE 4

Example 2 was repeated with the following modifications:

Instead of dextran sulfate, 1000 mg each of at least one of the following pharmaceuticals: adriblastin, endoxan, fluorouracil (as described by Brunner and Nagel, Internistische Krebstherapie; Springer-Verlag, 2nd edition, page 309, 1979) and colchicine (SIGMA) were added to the solution IV (see Example 1).

After adding the crosslinker and further processing as in Example 2, 1 mg of a monoclonal antibody JDB1 (as described by Strelkauskas, A. J., Cancer-Immunol. Immunother. Vol. 23, p. 31, 1986) was added to the vesicle solution VES to result in the following total composition for 1000 human doses of a pharmaceutical against mamma-carcinomas.

46 mg hemagglutinin 250 mg phosphatidylcholine 30 mg phosphatidylethanolamine 20 mg crosslinker (Sulfo-SMPB)

1 mg monoclonal antibody 1000 mg adriblastin 1000 mg endoxan 1000 mg fluoro-uracil

EXAMPLE 5

Examples 1 and 2 were repeated with the following modifications:

Instead of influenza hemagglutinin trimers, the monomers including the fusion peptide were used. The hemagglutinin-2-monomer containing the fusion peptide was obtained by cleavage of the S-H bridges by chemical reduction with D4-dithiothreitol (DTT, Sigma) and subsequent separation from the hemagglutinin-1 peptide by gel chromatography (Sephadex G 50) at pH 6. The purified hemagglutinin-2-monomer suspension contained 180 μg of monomers including the fusion peptide.

EXAMPLE 6

Figure 2:
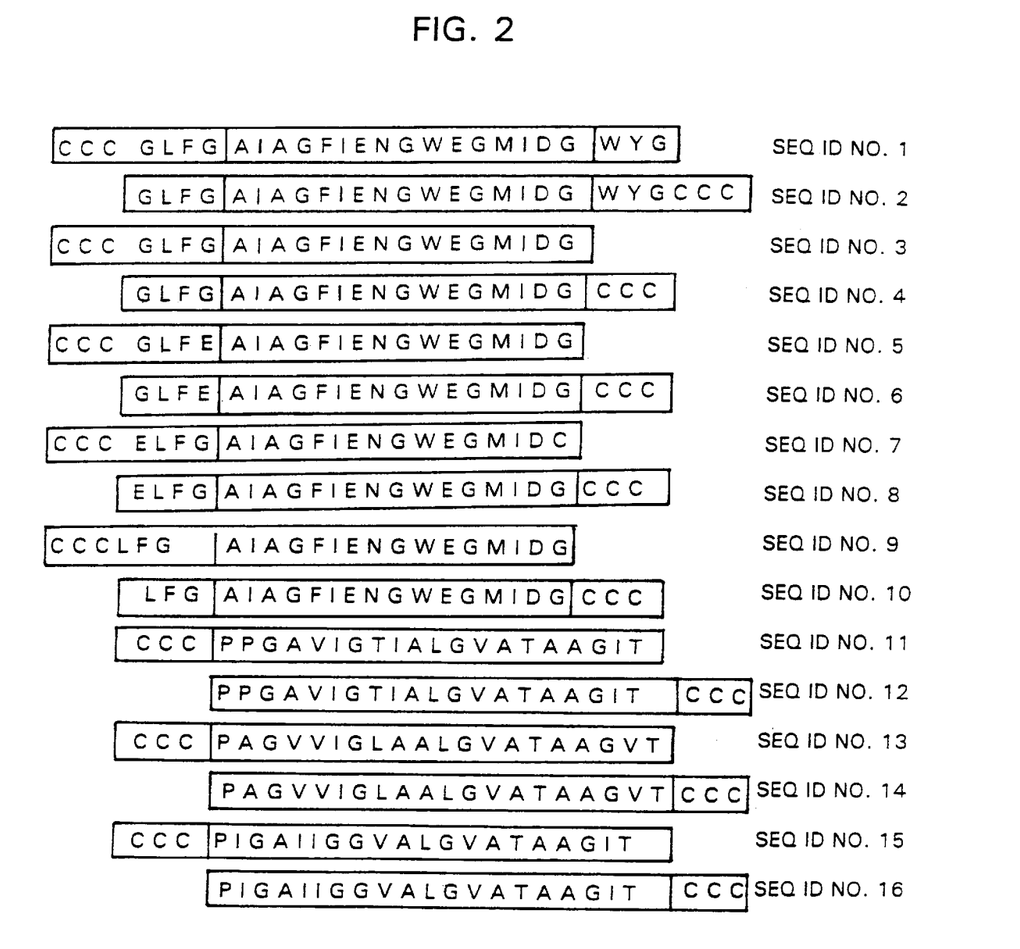

Example 2 was repeated with the following modifications:

Instead of influenza hemagglutinin trimers, the crude fusion peptide was used. The influenza fusion peptide used for preparation of synthetic membrane vesicles was obtained by chemical synthesis. Any one of the aminoacid sequences listed in FIG. 2 identified as SEQ ID NOS: 1–16, may be used. The arrangement of at least one, preferably three, cysteine groups at one end of the respective sequence has been found useful for the fusion activity.

The solution with one of these synthetic fusion peptides contained 4 μg per ml.

The vesicles containing one of the above fusion peptides have been prepared as follows:

9 mg of phosphatidylcholine and 1 mg of phosphatidylethanolamine per ml were dissolved in a 2:1 mixture of chloroform and methanol. 28 ml of this solution were carefully evaporated by applying a vacuum in a rotary evaporator forming a thin phospholipid layer on the inner surface of a round-bottom flask.

3 g of dextran sulfate were dissolved in 15.3 ml of a detergent solution containing 100 μmol of octaethylene glycol monododecyl ether per 1 ml of fusion buffer; the solution was then added to the phospholipid layer in the round-bottom flask. After shaking for at least 15 minutes and complete dissolution of the phospholipid layer, the solution was transferred to a glass container together with 4.8 g of polystyrene beaded microcarriers having a mesh size (wet) of 25–50.

The container was then shaken in such a way that the content moved twice per second from one end to the other. One hour later, the suspension was aspirated with a thin pipette and transferred to a new container with 2.4 g of polystyrene beaded microcarriers of the same size. The container was shaken for 30 minutes. This procedure was repeated twice. After the last step, the resulting solution was removed from the beads, fixed in a waterbath and treated with an ultrasonification apparatus (Bransonic, Branson Europe BV, frequency 50 kHz±10%). 10 seconds of ultrasonic shocks repeated twice, after intervals of 10 seconds each, yielded medium size vesicles with a diameter of about 50–100 nm.

2 ml of water containing 20 mg of sulfo-SMPB (Pierce) were added to the above suspension. After 1 hour at room temperature under gentle shaking, the vesicles were pelletted by 15 minutes of ultracentrifugation at 100,000×g.

2 ml of the solution containing the synthetic fusion peptide were added to the pellet. The resuspended material was carefully shaken for a few seconds every 5 minutes during 1 hour at room temperature. Finally, the material was pelletted again (to remove non-bonded fusion peptides) by ultracentrifugation at 100,000×g for 10 minutes. The pellet was resuspended in 200 ml of physiological NaCl solution.

EXAMPLE 7

Example 6 was repeated with the following modifications:

2 ml of a solution containing 2 μg of a synthetic fusion peptide and 2 ml containing 100 μg of Anti-Leu 3A were added to the pellet containing the vesicles. The resuspended material was carefully shaken for a few seconds every 5 minutes during one hour at room temperature. Finally, the material was pelletted again (to remove non-bonded fusion and cell specific peptides) by ultracentrifugation at 100,000×g for 10 minutes. The pellet was resuspended in 200 ml of physiological NaCl solution.

EXAMPLE 8

Vesicles according to Examples 1 through 4 were prepared with the fusion peptide or hemagglutinin from rhabdoviruses, parainfluenzaviruses or togaviruses.

a) The rhabdovirus rabies was produced in human diploid cells. The harvests (supernatants) containing 107 rabies viruses per ml were purified and concentrated by sucrose density ultracentrifugation. The purified rabies virus suspension contained 210 μg of rabies virus hemagglutinin per ml and was further processed according to Example 1.

b) The parainfluenza virus type III was grown in the allantoic cavity of hen eggs and was purified twice by ultracentrifugation in a sucrose gradient as in Example 1. The purified parainfluenza virion suspension contained 245 μg of parainfluenza virus hemagglutinin per ml and was further processed according to Example 1.

c) The togavirus rubella was produced in human diploid cells and purified according a). The purified rubella virion suspension contained 205 μg of rubella virus hemagglutinin per ml and was further processed according to Example 1.

EXAMPLE 9

Antiviral drugs were prepared according to Example 1. hu-PBL-SCID mice were treated for 14 days with ribonuclease dimer for 10 days alternatively with a phosphate buffer solution (blank test) only, with dextran sulfate or ribonuclease dimer (prepared according to Example 1 of PCT/US90/00141) at three dose levels, with dextran sulfate in liposomes, or ribonuclease dimer in liposomes, both latter prepared according to Example 1 of the present invention. Treatment was initiated at the same time as virus challenge with 100 TCID$_{50}$ of HIV-1$_{IIIB}$. hu-PBL-SCID mice were assessed for evidence of viral infection (virus isolation, PCR detection of proviral sequences) at 2, 4, and 6 weeks following viral infection. The results of the study show the percentage of animals in each treatment group from which virus was isolated:

| | |
|---|---|
| phosphate buffer solution (blank test) | 80% |
| ribonuclease dimer 0.001 mg/kg | 92% |
| ribonuclease dimer 0.1 mg/kg | 30% |
| ribonuclease dimer 10.0 mg/kg | 63% |
| dextran sulfate 10 mg/kg | 33% |
| dextran sulfate 10 mg/kg in liposomes | 14% |
| ribonuclease dimer in liposomes | 25% |

The study results indicate protection of the majority of treated hu-PBL-SCID mice from HIV infection following q. 12 hr. injection of 0.1 mg/kg ribonuclease dimer, 10 mg/kg dextran sulfate, liposomes containing ribonuclease dimer, and liposomes containing dextran sulfate. Protection was marginal with ribonuclease dimer at 10 mg/kg, which might be due to the fact that, at higher dosage levels, ribonuclease dimer suppresses immunity. No protective effect of ribonuclease dimer at 0.001 mg/kg was seen. However, with ribonuclease dimer in liposomes according to the present invention, the success rate improved from 63% to 25% in spite of the high dosage. Further improvement is expected from optimum dosage levels in liposomes.

The same conclusions hold when mice with poorly functioning human PBL grafts at the end of the experiment are excluded from analysis, although it appears from analysis of human immunoglobulin levels and β-globin PCR results that treatment with either ribonuclease dimer liposomes or dextran sulfate liposomes interfered with the survival of human cells. Exclusion of hu-PBL-SCID mice on the basis of human function allows some distinction between direct anti-viral effects and immunomodulatory activity.

EXAMPLE 10

Figure 3:
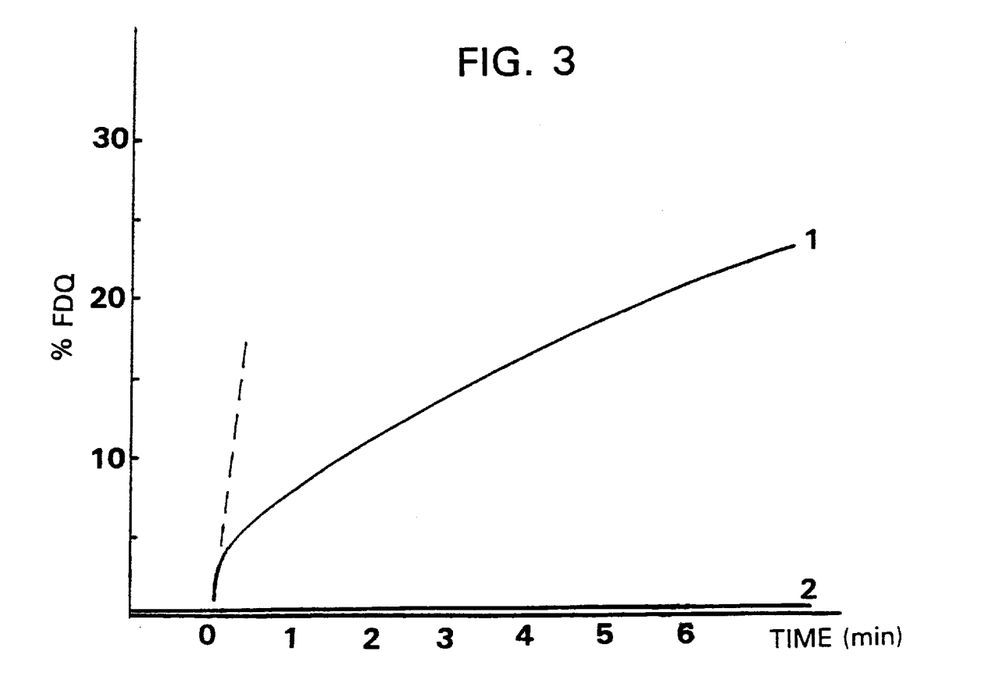

In a fusion test described by Lüscher and Glück (1990) (Antiviral Research 14, 39–50), vesicles prepared according to Example 1 were compared with reconstituted influenza vesicles prepared according to the method of Kawasaki et al. in fusion activity with model membranes:

FIG. 3 shows the kinetics of fluorescence de-quenching of R18-labelled influenza A virus with DOPC-cholesterol liposomes. The increase in fluorescence is expressed in % FDQ, calculated according to Lüscher & Glück (see above).

The initial fusion rates were obtained from the tangents to the fusion curves at time 0, when the fusion was initiated (dotted line in FIG. 3). Curve 2 corresponds to the fusion activity of vesicles prepared according to the method of Kawasaki et al.

We claim:

1. A phospholipid bilayer vesicle having at least one desired drug or pharmaceutically active substance therein, said vesicle comprising:
   (a) a membrane having one or more viral phospholipids in combination with other phospholipids comprising phosphatidylethanolamine (PE);
   (b) at least one active fusion peptide that is a non-Sendai viral hemagglutinin that causes the vesicles to be internalized by target cells through phagocytosis or endocytosis, said hemagglutinin being attached directly or indirectly to said membrane;

(c) a bifunctional crosslinker linked to phosphatidylethanolamine (PE) of said membrane; and (d) at least one cell-specific marker linked via its sulphur to the PE-bound crosslinker, said marker being a biologically active protein for binding to a receptor of target cells.

2. The vesicle according to claim 1, whose membrane comprises less than 1% cholesterol by weight.

3. The vesicle according to claim 1, wherein said vesicle has a diameter ranging from about 50 to 100 nm.

4. The vesicle according to claim 1, wherein the viral phospholipids are derived from at least one virus selected from the group consisting of influenza virus, rhabdovirus, parainfluenza virus type III, Semliki Forest virus and togavirus.

5. The vesicle according to claim 4, wherein the influenza virus is of the A-$H_1N_1$ subtype.

6. The vesicle according to claim 1, wherein the membrane includes:

70–95% by weight of phosphatidylcholine and 5 to 30% by weight of phosphatidylethanolamine, based on total phospholipids; and 5 to 10% by weight of said bifunctional crosslinker.

7. The vesicle according to claim 1, wherein the crosslinker is a sulfosuccinimidyl derivative.

8. The vesicle according to claim 1, wherein the cell-specific marker is a monoclonal antibody.

9. The vesicle according to claim 8, wherein said antibody is an IgG antibody.

10. The vesicle according to claim 1, wherein said other phospholipids further comprise phosphatidylcholine.

11. The vesicle according to claim 1, wherein the desired drug or pharmaceutically active substance is selected from the group consisting of dextran sulfate, ribonuclease dimer, lysozyme dimer, imidazole-carboxamide, hydroxy-urea, adriblastin, endoxan, fluoro-uracil, and colchicine.

12. The vesicle of claim 1, wherein said viral hemagglutinin is hemagglutinin derived from at least one virus selected from the group consisting of influenza virus, rhabdovirus, parainfluenza virus type III, Semliki Forest virus, and togavirus.

13. The vesicle of claim 1, wherein said viral hemagglutinin is hemagglutinin trimer of influenza virus.

14. The vesicle according to claim 1, wherein the bifunctional crosslinker is derived from a crosslinking organic molecule that comprises a carboxylic and a maleimido group.

15. The vesicle according to claim 14, wherein the organic molecule is sulfosuccinimidyl-4-(p-maleimidophenyl) butyrate (Sulfo-SMPB).

16. A phospholipid bilayer vesicle according to claim 1, wherein the phospholipids comprise 70–95% by weight of phosphatidylcholine and 5 to 30% by weight of phosphatidylethanolamine, based on total phospholipids, and wherein further the hemagglutinin is hemagglutinin trimer from influenza virus, the crosslinker is present in a concentration of 5 to 10% by weight and is derived from a crosslinking organic molecule that comprises a carboxylic and a maleimido group, and the cell-specific marker is a monoclonal antibody.

17. The vesicle according to claim 16, wherein the desired drug or pharmaceutically active substance is selected from the group consisting of dextran sulfate, ribonuclease dimer, lysozyme dimer, imidazole-carboxamide, hydroxy-urea, adriblastin, endoxan, fluoro-uracil, and colchicine.

18. The vesicle according to claim 1, wherein said other phospholipids further comprise phosphatidylcholine which is present in the membrane in a weight-ratio ranging from 1:2 to 1:100 of viral phospholipids:phosphatidylcholine.

19. A method of slowing the progression of cancer, comprising the step of:
   administering to a patient in need of such treatment an effective amount of pharmaceutical preparation comprising phospholipid bilayer vesicles as defined in any one of claim 1, 13 or 16, and wherein at least one anti-cancer drug is encapsulated in said vesicles and is administered to said patient at a dose of approximately 0.001 to 10 mg of drug per kg body weight.

20. The method according to claim 19, wherein said anti-cancer drug is selected from the group consisting of dextran sulfate, ribonuclease dimer, lysozyme dimer, imidazole-carboxamide, hydroxy-urea, adriblastin, endoxan, fluoro-uracil, and colchicine.

21. A method of prophylactic intervention or therapeutic treatment of a viral disease, comprising the step of:
   administering to a patient in need of such treatment an effective amount of pharmaceutical preparation comprising phospholipid bilayer vesicles as defined in any one of claim 1, 13 or 16 and wherein at least one anti-viral drug is encapsulated in said vesicles and is administered to said patient at a dose of approximately 0.001 to 10 mg of drug per kg body weight.

22. The method according to claim 21, wherein said antiviral drug is selected from the group consisting of dextran sulfate, ribonuclease dimer and lysozyme dimer.

23. A pharmaceutical composition, comprising a pharmaceutically acceptable carrier and an effective amount of a desired drug or pharmaceutically active substance encapsulated in a vesicle as defined in claim 1, 13 or 16, wherein the effective amount ranges from 0.001 to 10 mg of drug per kg body weight.

24. The pharmaceutical composition according to claim 23, wherein the desired drug or pharmaceutically active substance is selected from the group consisting of dextran sulfate, ribonuclease dimer, lysozyme dimer, imidazole-carboxamide, hydroxy-urea, adriblastin, endoxan, fluoro-uracil, and colchicine.

25. A process for the preparation of a phospholipid bilayer vesicle comprising at least one fusion peptide and at least one cell-specific marker on the membrane, and at least one desired drug or pharmaceutically active substance, said process comprising the steps of:
   (a) dissolving purified virus or parts thereof containing non-Sendai hemagglutinin that causes the vesicles to be internalized by target cells by phagocytosis or endocytosis, in a non-ionic detergent solution that does not react with hemagglutinin and that comprises octaethyleneglycol monododecylether;

(b) subjecting the solution resulting from step (a) to ultracentrifugation, and mixing the resulting supernatant which contains viral lipids and at least one hemagglutinin fusion peptide with said desired drug or substance;

(c) combining the mixture with other phospholipids, said other phospholipids comprising phosphatidylethanolamine;

(d) repeatedly treating the mixture from step (c) with microcarriers to remove the detergent whereby vesicles are formed;

(e) subjecting the vesicles resulting from step (d) to repeated ultrasonication to adjust the size of the vesicles;

(f) reacting the vesicles of step (c) with a bifunctional crosslinker for binding to phosphatidylethanolamine (PE) of the vesicle membrane and for binding polypeptides, and pelleting the vesicles; and (g) reacting the pelleted vesicles with a solution containing at least one cell-specific marker for binding to the PE-bound crosslinker, said marker being a biologically active protein for binding to a receptor of target cells.

26. The process according to claim 25, wherein the detergent solution comprises a fusion buffer and 10 to 250 μmol octaethyleneglycol monododecylether per ml.

27. The process according to claim 25, wherein the detergent solution comprises a fusion buffer and 80 to 120 μmol octaethyleneglycol monododecylether per ml.

28. The process according to claim 25, wherein the microcarriers are polystyrene beaded microcarriers having a wet mesh size of 20–50, and the solution under step (d) is treated four times with said microcarriers.

29. The process according to claim 25, wherein said cell-specific marker is an antibody.

30. The process of claim 25, wherein the crosslinker is a sulfosuccinimidyl derivative.

31. The process of claim 25, wherein the detergent is removed from the solution by the application of 1 to 2 g of polystyrene beaded microcarriers per 100 mg detergent.

32. The process of claim 25, wherein said other phospholipids added in step (c) further comprise phosphatidylcholine.

33. The process of claim 25, wherein said viral hemagglutinin is hemagglutinin derived from at least one virus selected from the group consisting of influenza virus, rhabdovirus, parainfluenza virus, Semliki Forest virus and togavirus.

34. The process of claim 25, wherein said viral hemagglutinin is hemagglutinin trimer of influenza virus.

35. The process according to claim 25, wherein the crosslinker is a crosslinking organic molecule that comprises a carboxylic and a maleimido group.

36. The process according to claim 35, wherein said organic molecule is a sulfosuccinimidyl-4-(p-maleimidophenyl)butyrate (Sulfo-SMPB).

37. A phospholipid bilayer vesicle comprising:

at least one fusion peptide and at least one cell-specific marker on a membrane; and at least one desired drug or pharmaceutically active substance, wherein the membrane includes (a) one or more viral phospholipids in combination with other phospholipids, the other phospholipids comprising phosphatidylethanolamine;

(b) at least one non-Sendai viral hemagglutinin, as a fusion peptide;

(c) a bifunctional crosslinker bound to said membrane containing said phosphatidylethanolamine, said crosslinker for binding polypeptides;

(d) at least one cell-specific marker linked via sulphur to the crosslinker, said marker being a protein which is further capable of linking to a receptor of cells inducing the endocytosis mechanism; and (e) cholesterol in a concentration of less than approximately 10% by weight.

38. The vesicle according to claim 37, wherein said other phospholipids further comprise phosphatidylcholine which is present in the membrane in a weight-ratio ranging from 1:2 to 1:100 of viral phospholipids:phosphatidylcholine.

39. A phospholipid bilayer vesicle of a structure that results from the steps of:

(a) dissolving purified virus or parts thereof containing non-Sendai hemagglutinin that causes the vesicles to be internalized by target cells by phagocytosis or endocytosis, in a non-ionic detergent solution that does not react with hemagglutinin and that comprises octaethyleneglycol monododecylether;

(b) subjecting the solution resulting from step (a) to ultracentrifugation, and mixing the resulting supernatant which contains viral lipids and at least one hemagglutinin fusion peptide with said desired drug or substance;

(c) combining the mixture with other phospholipids, said other phospholipids comprising phosphatidylethanolamine;

(d) repeatedly treating the mixture from step (c) with microcarriers to remove the detergent whereby vesicles are formed;

(e) subjecting the vesicles resulting from step (d) to repeated ultrasonication to adjust the size of the vesicles;

(f) reacting the vesicles of step (e) with a bifunctional crosslinker for binding to phosphatidylethanolamine (PE) of the vesicle membrane and for binding polypeptides, and pelleting the vesicles; and (g) reacting the pelleted vesicles with a solution containing at least one cell-specific marker for binding to the PE-bound crosslinker, said marker being a biologically active protein for binding to a receptor of target cells.

* * * * *

```
                          SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
          (A) LENGTH: 26 amino acids
          (B) TYPE: amino acid
          (C) STRANDEDNESS: single
          (D) TOPOLOGY: linear (vi) ORIGINAL SOURCE:
          (A) ORGANISM: myxovirus, paramyxovirus, rhabdovirus (xi) SEQUENCE DESCRIPTION: SEQ ID NO:1:

Cys Cys Cys Gly Leu Phe Gly Ala Ile Ala Gly Phe Ile Glu Asn Gly
     1               5                  10                  15

Trp Glu Gly Met Ile Asp Gly Trp Tyr Gly
                 20                  25

(2) INFORMATION FOR SEQ ID NO:2:

(i) SEQUENCE CHARACTERISTICS:
          (A) LENGTH: 26 amino acids
          (B) TYPE: amino acid
          (C) STRANDEDNESS: single
          (D) TOPOLOGY: linear (vi) ORIGINAL SOURCE:
          (A) ORGANISM: myxovirus, paramyxovirus, rhabdovirus (xi) SEQUENCE DESCRIPTION: SEQ ID NO:2:

Gly Leu Phe Gly Ala Ile Ala Gly Phe Ile Glu Asn Gly Trp Glu Gly
     1               5                  10                  15

Met Ile Asp Gly Trp Tyr Gly Cys Cys Cys
                 20                  25

(2) INFORMATION FOR SEQ ID NO:3:

(i) SEQUENCE CHARACTERISTICS:
          (A) LENGTH: 23 amino acids
          (B) TYPE: amino acid
          (C) STRANDEDNESS: single
          (D) TOPOLOGY: linear (vi) ORIGINAL SOURCE:
          (A) ORGANISM: myxovirus, paramyxovirus, rhabdovirus
```

(xi) SEQUENCE DESCRIPTION: SEQ ID NO:3:

Cys Cys Cys Gly Leu Phe Gly Ala Ile Ala Gly Phe Ile Glu Asn Gly
1               5                   10                  15

Trp Glu Gly Met Ile Asp Gly
            20

(2) INFORMATION FOR SEQ ID NO:4:

(i) SEQUENCE CHARACTERISTICS:
        (A) LENGTH: 23 amino acids
        (B) TYPE: amino acid
        (C) STRANDEDNESS: single
        (D) TOPOLOGY: linear (vi) ORIGINAL SOURCE:
        (A) ORGANISM: myxovirus, paramyxovirus, rhabdovirus (xi) SEQUENCE DESCRIPTION: SEQ ID NO:4:

Gly Leu Phe Gly Ala Ile Ala Gly Phe Ile Glu Asn Gly Trp Glu Gly
1               5                   10                  15

Met Ile Asp Gly Cys Cys Cys
            20

(2) INFORMATION FOR SEQ ID NO:5:

(i) SEQUENCE CHARACTERISTICS:
        (A) LENGTH: 23 amino acids
        (B) TYPE: amino acid
        (C) STRANDEDNESS: single
        (D) TOPOLOGY: linear (vi) ORIGINAL SOURCE:
        (A) ORGANISM: myxovirus, paramyxovirus, rhabdovirus (xi) SEQUENCE DESCRIPTION: SEQ ID NO:5:

Cys Cys Cys Gly Leu Phe Glu Ala Ile Ala Gly Phe Ile Glu Asn Gly
1               5                   10                  15

Trp Glu Gly Met Ile Asp Gly
            20

(2) INFORMATION FOR SEQ ID NO:6:

(i) SEQUENCE CHARACTERISTICS:
        (A) LENGTH: 23 amino acids
        (B) TYPE: amino acid
        (C) STRANDEDNESS: single
        (D) TOPOLOGY: linear (vi) ORIGINAL SOURCE:
        (A) ORGANISM: myxovirus, paramyxovirus, rhabdovirus (xi) SEQUENCE DESCRIPTION: SEQ ID NO:6:

Gly Leu Phe Glu Ala Ile Ala Gly Phe Ile Glu Asn Gly Trp Glu Gly
1               5                   10                  15

Met Ile Asp Gly Cys Cys Cys
            20

(2) INFORMATION FOR SEQ ID NO:7:

(i) SEQUENCE CHARACTERISTICS:
        (A) LENGTH: 23 amino acids
        (B) TYPE: amino acid
        (C) STRANDEDNESS: single
        (D) TOPOLOGY: linear (vi) ORIGINAL SOURCE:

```
        (A) ORGANISM: myxovirus, paramyxovirus, rhabdovirus (xi) SEQUENCE DESCRIPTION: SEQ ID NO:7:

Cys Cys Cys Glu Leu Phe Gly Ala Ile Ala Gly Phe Ile Glu Asn Gly
    1               5                   10                  15

Trp Glu Gly Met Ile Asp Gly
                20

(2) INFORMATION FOR SEQ ID NO:8:

(i) SEQUENCE CHARACTERISTICS:
        (A) LENGTH: 23 amino acids
        (B) TYPE: amino acid
        (C) STRANDEDNESS: single
        (D) TOPOLOGY: linear (vi) ORIGINAL SOURCE:
        (A) ORGANISM: myxovirus, paramyxovirus, rhabdovirus (xi) SEQUENCE DESCRIPTION: SEQ ID NO:8:

Glu Leu Phe Gly Ala Ile Ala Gly Phe Ile Glu Asn Gly Trp Glu Gly
    1               5                   10                  15

Met Ile Asp Gly Cys Cys Cys
                20

(2) INFORMATION FOR SEQ ID NO:9:

(i) SEQUENCE CHARACTERISTICS:
        (A) LENGTH: 22 amino acids
        (B) TYPE: amino acid
        (C) STRANDEDNESS: single
        (D) TOPOLOGY: linear (vi) ORIGINAL SOURCE:
        (A) ORGANISM: myxovirus, paramyxovirus, rhabdovirus (xi) SEQUENCE DESCRIPTION: SEQ ID NO:9:

Cys Cys Cys Leu Phe Gly Ala Ile Ala Gly Phe Ile Glu Asn Gly Trp
    1               5                   10                  15

Glu Gly Met Ile Asp Gly
                20

(2) INFORMATION FOR SEQ ID NO:10:

(i) SEQUENCE CHARACTERISTICS:
        (A) LENGTH: 22 amino acids
        (B) TYPE: amino acid
        (C) STRANDEDNESS: single
        (D) TOPOLOGY: linear (vi) ORIGINAL SOURCE:
        (A) ORGANISM: myxovirus, paramyxovirus, rhabdovirus (xi) SEQUENCE DESCRIPTION: SEQ ID NO:10:

Leu Phe Gly Ala Ile Ala Gly Phe Ile Glu Asn Gly Trp Glu Gly Met
    1               5                   10                  15

Ile Asp Gly Cys Cys Cys
                20

(2) INFORMATION FOR SEQ ID NO:11:

(i) SEQUENCE CHARACTERISTICS:
        (A) LENGTH: 23 amino acids
        (B) TYPE: amino acid
        (C) STRANDEDNESS: single
        (D) TOPOLOGY: linear
```

(vi) ORIGINAL SOURCE:
            (A) ORGANISM: myxovirus, paramyxovirus, rhabdovirus (xi) SEQUENCE DESCRIPTION: SEQ ID NO:11:

Cys Cys Cys Pro Pro Gly Ala Val Ile Gly Thr Ile Ala Leu Gly Val
        1               5                   10                  15

Ala Thr Ala Ala Gly Ile Thr
                    20

(2) INFORMATION FOR SEQ ID NO:12:

(i) SEQUENCE CHARACTERISTICS:
            (A) LENGTH: 23 amino acids
            (B) TYPE: amino acid
            (C) STRANDEDNESS: single
            (D) TOPOLOGY: linear (vi) ORIGINAL SOURCE:
            (A) ORGANISM: myxovirus, paramyxovirus, rhabdovirus (xi) SEQUENCE DESCRIPTION: SEQ ID NO:12:

Pro Pro Gly Ala Val Ile Gly Thr Ile Ala Leu Gly Val Ala Thr Ala
        1               5                   10                  15

Ala Gly Ile Thr Cys Cys Cys
                    20

(2) INFORMATION FOR SEQ ID NO:13:

(i) SEQUENCE CHARACTERISTICS:
            (A) LENGTH: 23 amino acids
            (B) TYPE: amino acid
            (C) STRANDEDNESS: single
            (D) TOPOLOGY: linear (vi) ORIGINAL SOURCE:
            (A) ORGANISM: myxovirus, paramyxovirus, rhabdovirus (xi) SEQUENCE DESCRIPTION: SEQ ID NO:13:

Cys Cys Cys Pro Ala Gly Val Val Ile Gly Leu Ala Ala Leu Gly Val
        1               5                   10                  15

Ala Thr Ala Ala Gly Val Thr
                    20

(2) INFORMATION FOR SEQ ID NO:14:

(i) SEQUENCE CHARACTERISTICS:
            (A) LENGTH: 23 amino acids
            (B) TYPE: amino acid
            (C) STRANDEDNESS: single
            (D) TOPOLOGY: linear (vi) ORIGINAL SOURCE:
            (A) ORGANISM: myxovirus, paramyxovirus, rhabdovirus (xi) SEQUENCE DESCRIPTION: SEQ ID NO:14:

Pro Ala Gly Val Val Ile Gly Leu Ala Ala Leu Gly Val Ala Thr Ala
        1               5                   10                  15

Ala Gly Val Thr Cys Cys Cys
                    20

(2) INFORMATION FOR SEQ ID NO:15:

(i) SEQUENCE CHARACTERISTICS:
            (A) LENGTH: 23 amino acids
            (B) TYPE: amino acid
            (C) STRANDEDNESS: single
            (D) TOPOLOGY: linear -continued

```
    (vi) ORIGINAL SOURCE:
         (A) ORGANISM: myxovirus, paramyxovirus, rhabdovirus (xi) SEQUENCE DESCRIPTION: SEQ ID NO:15:

Cys Cys Cys Pro Ile Gly Ala Ile Ile Gly Gly Val Ala Leu Gly Val
    1               5                   10                  15

Ala Thr Ala Ala Gly Ile Thr
                20

(2) INFORMATION FOR SEQ ID NO:16:

(i) SEQUENCE CHARACTERISTICS:
         (A) LENGTH: 23 amino acids
         (B) TYPE: amino acid
         (C) STRANDEDNESS: single
         (D) TOPOLOGY: linear (vi) ORIGINAL SOURCE:
         (A) ORGANISM: myxovirus, paramyxovirus, rhabdovirus (xi) SEQUENCE DESCRIPTION: SEQ ID NO:16:

Pro Ile Gly Ala Ile Ile Gly Gly Val Ala Leu Gly Val Ala Thr Ala
    1               5                   10                  15

Ala Gly Ile Thr Cys Cys Cys
                20
```